United States Patent [19]

Heubach et al.

[11] 4,239,525
[45] Dec. 16, 1980

[54] 1,2,4-TRIAZOLE DERIVATIVES

[75] Inventors: Günther Heubach; Burkhard Sachse, both of Kelkheim; Helmut Bürstell, Frankfurt am Main, all of Fed. Rep. of Germany

[73] Assignee: Hoechst Aktiengesellschaft, Frankfurt am Main, Fed. Rep. of Germany

[21] Appl. No.: 49,437

[22] Filed: Jun. 18, 1979

[30] Foreign Application Priority Data

Jun. 19, 1978 [DE] Fed. Rep. of Germany ....... 2826760

[51] Int. Cl.³ .................... A01N 43/82; C07D 249/08
[52] U.S. Cl. ....................................... 71/92; 424/269; 548/262; 542/421; 542/427; 542/426
[58] Field of Search .................... 260/308 R; 542/421, 542/426, 427; 424/269; 71/92

[56] References Cited

U.S. PATENT DOCUMENTS

| | | | |
|---|---|---|---|
| 3,736,330 | 5/1973 | Haken | 260/308 R |
| 3,872,117 | 3/1975 | Meiser et al. | 548/341 |
| 4,086,351 | 4/1978 | Balasubramanyan et al. | 260/308 R |

*Primary Examiner*—Alton D. Rollins
*Attorney, Agent, or Firm*—Curtis, Morris & Safford

[57] ABSTRACT

1,2,4-Triazole derivatives of the formula

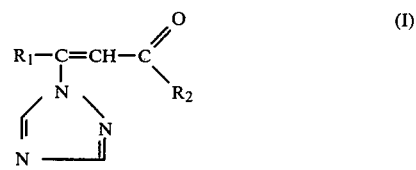

in which
 $R_1$ denotes methyl or optionally substituted phenyl,
 $R_2$ denotes $R_3O-$ in which $R_3$ is optionally substituted alkyl, alkinyl preferably having up to 3 carbon atoms, optionally substituted cycloalkyl, optionally substituted phenyl, or
 $R_2$ denotes

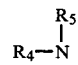

in which $R_4$ is hydrogen or optionally substituted $(C_1-C_4)$ alkyl and $R_5$ is $(C_1-C_4)$alkyl or optionally substituted phenyl are effective as fungicides and growth regulators.

8 Claims, No Drawings

1,2,4-TRIAZOLE DERIVATIVES

This invention relates to novel 1,2,4-triazole derivatives, to their manufacture and their use as pesticides in plant protection and as agents for the regulation of growths of plants.

The compounds according to the invention have the formula I

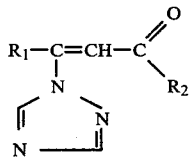

in which

R$_1$ denotes methyl or phenyl optionally substituted by halogen, (C$_1$-C$_4$)alkyl, preferably (C$_1$-C$_2$)alkyl, or (C$_1$-C$_4$)alkoxy, preferably (C$_1$-C$_2$)alkoxy and R$_2$ denotes the group R$_3$O— in which R$_3$ is alkyl, preferably having up to 12 carbon atoms and more preferably up to 8 carbon atoms, which may be substituted additionally by halogen, preferably chlorine or bromine, (C$_1$-C$_4$)alkoxy or alkoxycarbonyl preferably having up to 8 carbon atoms, more preferably up to 5 carbon atoms; or is alkinyl preferably having up to 3 carbon atoms; or is cycloalkyl preferably having up to 6 carbon atoms and optionally substituted additionally by (C$_1$-C$_4$)alkyl; or is phenyl optionally substituted by halogen or F$_3$C—, or R$_2$ denotes

in which R$_4$ is hydrogen or (C$_1$-C$_4$)alkyl optionally substituted by alkoxycarbonyl preferably having up to 8 carbon atoms, more preferably up to 5 carbon atoms and R$_5$ is (C$_1$-C$_4$)alkyl or phenyl optionally substituted by halogen, F$_3$C—, (C$_1$-C$_4$)alkyl, (C$_1$-C$_4$)alkoxy, phenoxy or halophenoxy.

In general, the compounds of formula I are obtained in the form of mixtures of cis/trans isomers which can be separated into the individual isomers by known methods.

The triazole derivatives of formula I can be produced by reacting a compound of the formula II

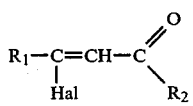

in which R$_1$ and R$_2$ are as defined under formula I and Hal is chlorine or bromine, preferably chlorine, at elevated temperature, preferably of from 70° to 140° C. and more preferably 80° to 110° C., with 1,2,4-triazole in the presence of an agent binding hydrogen halide. The reaction is preferably carried out in an organic solvent, for example acetone, acetonitrile, dimethyl formamide or higher boiling hydrocarbons, for example xylene. To bind the hydrohalic acid formed in the reaction it proved advantageous to use an at least molar excess of the triazole or a corresponding amount of an inorganic or tertiary organic base, for example K$_2$CO$_3$, Na$_2$CO$_3$, triethylamine, pyridine or N,N-dimethylaniline.

The starting compounds of formula II which, for the most part, are also novel, can be produced in known manner from acid chlorides of the formula III

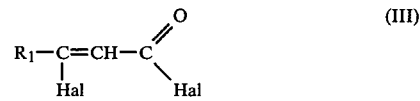

by reaction with alcohols of the formula R$_2$OH or amines of the formula

in which formulae R$_1$, R$_2$, R$_4$, R$_5$ and Hal are as defined under formulae I and II.

The carboxylic acid chlorides of formula III can be produced by processes known from literature, for example by reacting a β-keto ester of the formula R$_1$—CO—CH$_2$—COOR with a chlorination agent (cf. JACS 77, 1137 (1955); J. Chem. Soc. 99, page 1621 (1911)).

The compounds of formula I are distinguished by a very good fungicidal effect. They can be used to combat curatively fungi that have already penetrated into the vegetal tissue. This is especially important and advantageous with fungal diseases which can no longer be combated with the usual fungicides once the infection has started. The compounds of the invention are effective, for example, against Phytophthora infestans, Plasmopara viticola, Venturia inaequalis, Cercospora betae and Tilletia tritici and above all, against types of genuine mildew in the cultivation of fruit, vegetable, cereals and vine and in horticulture. In part, they are also effective against rust fungi. It should be noted that the compounds of the invention have an outstanding effect against types of mildew that are resistant to benzimidazole derivatives, for example Benomyl and Carbendazim.

The compounds of formula I according to the invention can also be used in the technical field, for example in wood protecting agents, for paints, as preservatives, for example in lubricating cooling liquids for shaving metal. Moreover, some of the compounds exhibit a good effect against phytopathogeneous bacteria, the control of which increases in importance in horticulture and agriculture.

In biological experiments the compounds of formula I according to the invention exhibit very good growth regulating properties in a series of economically important plants. It should be noted especially that besides a general growth regulating effect, the compounds have a good growth inhibiting effect in cereals.

It has been proposed to regulate the growth of higher plants by the application of succinic acid 2,2-dimethylhydrazide, 2-chloroethyltrimethylammonium chloride and maleic acid hydrazide. The effect of these compounds is, however, not always satisfactory, for example, in that higher concentrations partially cause phytotoxic damages, the known compounds are ineffective in some important crop plants or the crop yield is impaired. In contradistinction thereto, the compounds of formula I according to the invention surprisingly exhibit an outstanding regulatory effect without phytotoxic damages occurring.

In plant protection the compounds of formula I can be used in the form of the usual formulations such as dusts, wettable powders, seed treating agents, dispersions, solutions, or emulsion concentrates. In general, the formulations contain from 2 to 95%, preferably 10 to 90% by weight of active compound of formula I. In addition, the formulations may contain the usual adhesives, wetting agents, dispersing agents, emulsifiers, penetration agents, solvents, fillers and carriers.

The following examples illustrate the invention.

(A) EXAMPLES OF PREPARATION

EXAMPLE 1

3-(1,2,4-Triazol-1-yl)-cinnamic acid-N-isopropyl-2',6'-dimethyl anilide

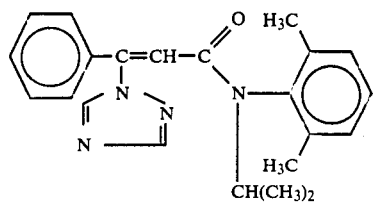

0.07 Mol (22.9 g) of 3-chloro-cinnamic acid N-isopropyl-2',6'-dimethyl anilide were dissolved in 90 ml of dimethyl formamide, 5.8 g (0.084 mol) of 1,2,4-triazole and 11.5 g of anhydrous potassium carbonate were added and the whole was kept for 6 hours at 100° C. while stirring. After cooling of the reaction mixture and pouring into iced water, it was extracted with methylene chloride and the organic phase was washed with water. After removal of the methylene chloride under reduced pressure, 23.6 g of an amber-colored, semicrystalline product were obtained which, according to thin layer chromatography, consisted of approximately equal parts of cis- and trans-isomer of 3-(1,2,4-triazol-1-yl)-cinnamic acid N-isopropyl-2',6'-dimethyl anilide.

Yield 23.6 g=93.5% of the theory. Thin layer chromatogram: $R_f$ 0.4 and 0.5. (pre-fabricated plates of silica gel 60 $F_{254}$ of Messrs. Merck). eluent: ethyl acetate. Analysis: $C_{22}H_{24}N_4O$; MW 360.4. calculated C 73.30%; H 6.71%; N 15.54%. found C 73.2%; H 6.7%; N 15.5%.

After recrystallization of a sample of toluene/gasoline, colorless crystals melting at 160° to 161° C. and having correct analytical values were obtained. NMR spectrum and thin layer chromatogram indicated a strong enrichment of one of the two isomers.

EXAMPLE 2

3-(1,2,4-Triazol-1-yl)-4'-chloro-cinnamic acid isobutyl ester

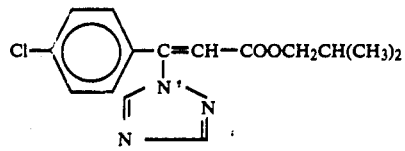

0.07 Mol (19.1 g) of 3-chloro-4'-chlorocinnamic acid isobutyl ester was reacted with 1,2,4-triazole under the conditions of Example 1. After working up, a honeycolored viscous sirup was obtained which, according to thin layer chromatography (eluent toluene/ethyl acetate 2:1); $R_f$ values 0.38 and 0.45 consisted of a mixture of cis- and trans-isomers of 3-(1,2,4-triazol-1-yl)-4'-chlorocinnamic acid isobutyl ester.

Yield 19.5 g=91% of the theory. Analysis: $C_{15}H_{16}ClN_3O_2$; MW 305.7. calculated C 58.92%; H 5.27%; N 13.74%. found C 58.6%; H 5.0% N 13.5%.

EXAMPLE 3

3-(1,2,4-Triazol-1-yl)-crotonic acid isobutyl ester

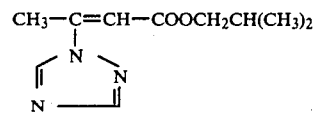

0.1 Mol (17.7 g) of 3-chlorocrotonic acid isobutyl ester in 100 ml acetonitrile, 012 mol (8.3 g) of 1,2,4-triazole and 0.12 mol (16.5 g) of anhydrous potassium carbonate were refluxed for 5 hours. After removal of the solvent under reduced presure, the reaction mixture was cooled, water was added and the resulting mixture was extracted with methylene chloride. After distillation of the methylene chloride under reduced pressure, the 3-(1,2,4-triazol-1-yl)-crotonic acid isobutyl ester was obtained in the form of a weakly yellow oil.

Yield 18.2 g=87% of the theory. Thin layer chromatogram (toluene/ethyl acetate 2:1). $R_f$ 0.2. Analysis: $C_{10}H_{15}N_3O_2$; MW 209.2. calculated C 57.40%; H 7.23%; N 20.08%. found C 57.1%; H 7.3%; N 19.8%.

EXAMPLES 4 to 90

Examples 4 to 6 were carried out in the manner described in Example 3 while Examples 7 to 90 were carried out under the conditions of Example 1. In the following table are indicated the radicals $R_1$ and $R_2$ of the compounds prepared from corresponding compounds of formula II and the melting points or the refractive index of said compounds.

TABLE 1 formula I

| Example No. | $R_1$ | $R_2$ | m.p. (°C.) |
|---|---|---|---|

TABLE 1-continued formula I $$R_1-\underset{\underset{\underset{N\equiv N}{\underset{|}{N}}}{|}}{C}=CH-\overset{O}{\overset{\|}{C}}-R_2$$

| | $R_1$ | $R_2$ | m.p. °C |
|---|---|---|---|
| 4 | —CH₃ | Cl—C₆H₃(—O—) [4-Cl, phenoxy] | 106–107 |
| 5 | —CH₃ | (CH₃)₂CHO— | 42–44 |
| 6 | —CH₃ | CH₃(CH₂)₃O— | 0.3/105 oil |
| 7 | —C₆H₅ | CH₃O— | 74–88 |
| 8 | —C₆H₅ | C₂H₅O— | oil |
| 9 | —C₆H₅ | (CH₃)₂CHO— | 0,3/147 |
| 10 | —C₆H₅ | CH₃CH₂CH₂O— | oil |
| 11 | —C₆H₅ | (CH₃)₂CHCH₂O— | oil |
| 12 | —C₆H₅ | CH₃(CH₂)₃O— | oil |
| 13 | —C₆H₅ | (CH₃)₃CO— | semi-crystalline |
| 14 | —C₆H₅ | C₆H₁₁—O— (cyclohexyloxy) | oil |
| 15 | —C₆H₅ | H₅C₂OOC—CH(CH₃)—O— | oil |
| 16 | —C₆H₅ | CH≡C—CH₂O— | oil |
| 17 | —C₆H₅ | C₆H₅—O— | 99–115 |
| 18 | —C₆H₅ | Cl—C₆H₃(—O—) | 108–121 (138–140)(+) |
| 19 | —C₆H₅ | —N(C₂H₅)₂ | oil |
| 20 | —C₆H₅ | —N(CH₂CH₂CH₃)₂ | oil |
| 21 | —C₆H₅ | —N[CH(CH₃)₂]₂ | 150–151 |
| 22 | —C₆H₅ | —NHCH(CH₃)₂ | 160–162 |
| 23 | —C₆H₅ | —NH—(2,6-(CH₃)₂C₆H₃) | 243–255 (265–266)(+) |
| 24 | —C₆H₅ | —N(CH(CH₃)₂)(C₆H₅) | sirup |
| 25 | —C₆H₅ | —N(CH(CH₃)₂)(4-Cl-C₆H₄) | oil |
| 26 | —C₆H₅ | —N(CH(CH₃)₂)(3-CF₃-C₆H₄) | oil |

TABLE 1-continued $$R_1-\underset{\underset{\underset{N\overset{\diagdown}{=}\!\!\!\diagup N}{|}}{N}}{C}=CH-\overset{O}{\overset{\|}{C}}-R_2 \quad \text{formula I}$$

| | R₁ | R₂ | |
|---|---|---|---|
| 27 |  | —N(C₂H₅)(2,6-di-C₂H₅-C₆H₃), CH(CH₃)₂ | sirup |
| 28 | 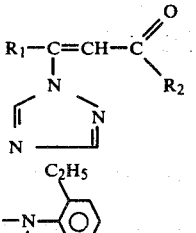 | —N(C₂H₅)(2,6-di-CH(CH₃)₂-C₆H₃), CH(CH₃)₂ | sirup |
| 29 |  | —N(CH(CH₃)₂)(2,6-di-CH(CH₃)₂-C₆H₃), CH(CH₃)₂ | 113–119 |
| 30 | 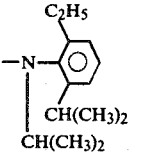 | —N(C₂H₅)(2,6-di-C₂H₅-C₆H₃), CH₂-(tetrahydrofuran-2-yl) | sirup |
| 31 |  | —N(CH₃)(2,6-di-CH₃-C₆H₃), CHCH₃COOC₂H₅ | semi-crystalline |
| 32 |  | —N(C₂H₅)(2,6-di-C₂H₅-C₆H₃), CH₂COOC₂H₅ | sirup |
| 33 | 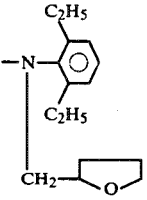 | —N(C₂H₅)(2,6-di-C₂H₅-C₆H₃), CHCH₃COOC₂H₅ | sirup |
| 34 |  | —O(CH₂)₂CH₃ | semi-crystalline |
| 35 |  | —OCH(CH₃)₂ | oil |
| 36 | 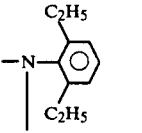 | —O(CH₂)₃CH₃ | semi-crystalline (100–104)⁽⁺⁾ |
| 37 |  | —O—C(CH₃)₃ | sirup |
| 38 | 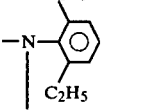 | —N(CH₃)(2,6-di-CH₃-C₆H₃), CH(CH₃)₂ | 104–122 (122–133)⁽⁺⁾ |

TABLE 1-continued formula I $$R_1-C=CH-C(=O)-R_2$$ with N-triazole substituent

| No. | $R_1$ | $R_2$ | m.p. (°C) |
|---|---|---|---|
| 39 | 4-Cl-C$_6$H$_4$- | -N(CH(CH$_3$)$_2$)-(2-C$_2$H$_5$-6-CH(CH$_3$)$_2$-C$_6$H$_3$) | sirup |
| 40 | 4-Cl-C$_6$H$_4$- | -N(CHCH$_3$COOC$_2$H$_5$)-(2,6-(CH$_3$)$_2$-C$_6$H$_3$) | sirup |
| 41 | 4-Br-C$_6$H$_4$- | -N(CH(CH$_3$)$_2$)-(2,6-(CH$_3$)$_2$-C$_6$H$_3$) | semi-crystalline (163–164)(+) |
| 42 | C$_6$H$_5$- | -N(CH(CH$_3$)$_2$)-(4-(2,4-Cl$_2$-C$_6$H$_3$O)-C$_6$H$_4$) | sirup |
| 43 | 4-Cl-C$_6$H$_4$- | -N(CH(CH$_3$)$_2$)-(2,6-(CH(CH$_3$)$_2$)$_2$-C$_6$H$_3$) | 129–157 |
| 44 | 4-Cl-C$_6$H$_4$- | -N(CH(CH$_3$)$_2$)-(4-(2,4-Cl$_2$-C$_6$H$_3$O)-C$_6$H$_4$) | sirup |
| 45 | 4-Cl-C$_6$H$_4$- | -OCH$_3$ | 117–122 |
| 46 | 4-Cl-C$_6$H$_4$- | -OC$_2$H$_5$ | semi-crystalline |
| 47 | 4-CH$_3$-C$_6$H$_4$- | -N(CH(CH$_3$)$_2$)-(2,6-(CH$_3$)$_2$-C$_6$H$_3$) | 105–135 |
| 48 | 4-CH$_3$-C$_6$H$_4$- | -O(CH$_2$)$_3$CH$_3$ | sirup |
| 49 | 4-Cl-C$_6$H$_4$- | -O-C$_6$H$_{11}$ | sirup |
| 50 | 4-Cl-C$_6$H$_4$- | -N(CH(CH$_3$)$_2$)-(3-CF$_3$-C$_6$H$_4$) | sirup |
| 51 | 4-Cl-C$_6$H$_4$- | -N(CH$_2$CH$_2$CH$_3$)$_2$ | 117–120 |
| 52 | 4-H$_3$CO-C$_6$H$_4$- | -O-(CH$_2$)$_3$CH$_3$ | oil |

TABLE 1-continued formula I:
$$R_1-C(=CH-C(=O)R_2)-N(\text{-triazolyl})$$

| Example No. | $R_1$ | $R_2$ | |
|---|---|---|---|
| 53 | H₃CO—C₆H₄— | —N(CH(CH₃)₂)(2,6-dimethylphenyl) with H₃C, CH₃ on ring | sirup |
| 54 | Cl—C₆H₄— | —O—(CH₂)₄—CH₃ | sirup |
| 55 | Cl—C₆H₄— | —O—(CH₂)₅—CH₃ | semicrystalline |
| 56 | Cl—C₆H₄— | —O—(CH₂)₂—CH(CH₃)—CH₃ | sirup |

| Example No. | $R_1$ | $R_2$ | $n_D^{30}$ (refractive index; not measured with viscous sirupy products) |
|---|---|---|---|
| 57 | Cl—C₆H₄— | —N(CH(CH₃)(C₂H₅))(2-methylphenyl) | 1.5779 |
| 58 | Cl—C₆H₄— | —N(CH(CH₃)(C₂H₅))(2-methoxyphenyl) | 1.5798 |
| 59 | Cl—C₆H₄— | —N(CH₃)(2-methylphenyl) | 1.5926 |
| 60 | Cl—C₆H₄— | —N(C₂H₅)(2-methylphenyl) | 1.5859 |
| 61 | H₃C—C₆H₄— | —N(CH(CH₃)₂)(2-methylphenyl) | 1.5688 |
| 62 | H₃C—C₆H₄— | —N(CH(CH₃)₂)(2-methoxyphenyl) | 1.5755 |
| 63 | Cl—C₆H₄— | —N(CH(CH₃)₂)(2-isopropylphenyl) | 1.5768 |
| 64 | H₃C—C₆H₄— | —N(CH(CH₃)₂)(2,6-diethylphenyl) | 1.5843 |
| 65 | H₃C—C₆H₄— | —N(CH(CH₃)₂)(3-trifluoromethylphenyl) | 1.5532 |

TABLE 1-continued formula I $$R_1-\underset{\underset{\underset{N\underset{\diagup}{=}}{|}}{\overset{|}{N}\underset{\diagdown}{=}N}}{C}=CH-\underset{\underset{R_2}{\|}}{\overset{O}{C}}$$

| No. | $R_1$ | $R_2$ | $n_D$ |
|---|---|---|---|
| 66 | 4-H$_3$C-C$_6$H$_4$- | —OCH(CH$_3$)$_2$ | 1.5587 |
| 67 | 4-H$_3$C-C$_6$H$_4$- | —OCHCH$_2$CH(CH$_3$)$_2$<br>   $\|$<br>   CH$_3$ | 1.5501 |
| 68 | 4-H$_3$C-C$_6$H$_4$- | —O(CH$_2$)$_2$CH$_3$ | 1.5602 |
| 69 | 3-Cl-C$_6$H$_4$- | —OCH(CH$_3$)$_2$ | 1.5583 |
| 70 | 3-Cl-C$_6$H$_4$- | —OCH$_2$CH(CH$_3$)$_2$ | 1.5372 |
| 71 | 3-Cl-C$_6$H$_4$- | —O(CH$_2$)$_2$CH$_3$ | 1.5682 |
| 72 | 4-Cl-C$_6$H$_4$- | —N(CH(CH$_3$)$_2$)(2-Cl-4-CH$_3$-C$_6$H$_3$) | 1.5812 |
| 73 | 4-Cl-C$_6$H$_4$- | —N(CH(CH$_3$)$_2$)(2,4-Cl$_2$-C$_6$H$_3$) | 1.5863 |
| 74 | 4-Cl-C$_6$H$_4$- | —N(CH(CH$_3$)$_2$)(3-OCH$_3$-C$_6$H$_4$) | sirup |
| 75 | 4-Cl-C$_6$H$_4$- | —N(CH(CH$_3$)$_2$)(4-Cl-2-OCH$_3$-C$_6$H$_3$) | sirup |
| 76 | 4-Cl-C$_6$H$_4$- | —N(CH(CH$_3$)$_2$)(4-CH(CH$_3$)$_2$-C$_6$H$_4$) | sirup |
| 77 | 4-Cl-C$_6$H$_4$- | —N(CH(CH$_3$)$_2$)(4-C$_2$H$_5$-C$_6$H$_4$) | semicrystalline |
| 78 | 4-Cl-C$_6$H$_4$- | —N(CH(CH$_3$)$_2$)(2-OCH$_3$-C$_6$H$_4$) | semicrystalline |
| 79 | 4-Cl-C$_6$H$_4$- | —N(CH(CH$_3$)$_2$)(4-OCH$_3$-C$_6$H$_4$) | sirup |

TABLE 1-continued formula I $$R_1-\underset{\underset{N\!=\!\!\!=\!\!N}{\overset{|}{N}}}{C}=CH-\overset{O}{\overset{\|}{C}}-R_2$$

| | $R_1$ | $R_2$ | (+) |
|---|---|---|---|
| 80 | Cl—C₆H₄— | —N(CH(CH₃)₂)—C₆H₄(CH₃) | 1.5328 |
| 81 | Cl—C₆H₄— | —N(CH(CH₃)₂)—C₆H₄(CH₃) | sirup |
| 82 | Cl—C₆H₄— | —N(CH(CH₃)₂)—C₆H₃Cl₂ | semicrystalline |
| 83 | Cl—C₆H₄— | —N(CH(CH₃)₂)—C₆H₄(C₂H₅) | sirup |
| 84 | Cl—C₆H₄— | —OCH₂CH(C₂H₅)(CH₂)₃CH₃ | sirup |
| 85 | Cl—C₆H₄— | —OCH(CH₃)CH₂CH(CH₃)₂ | sirup |
| 86 | Cl—C₆H₄— | O—(CH₂)₇CH₃ | semicrystalline |
| 87 | Cl—C₆H₄— | —O(CH₂)₂OC₂H₅ | sirup |
| 88 | Cl—C₆H₄— | —O(CH₂)₃Cl | sirup |
| 89 | Cl—C₆H₄— | —N(CH(CH₃)₂)—C₆H₄—OC₂H₅ | 1.5789 |
| 90 | Cl—C₆H₄— | —N(CH(CH₃)₂)—C₆H₄Cl | semicrystalline |

(+) melting point of samples recrystallized from toluene/hexane

(B) EXAMPLES OF FORMULATION

EXAMPLE A

A dusting powder is obtained by mixing
10 parts by weight of active substance and
90 parts by weight of talc as inert material and comminuting the mixture in a hammer mill.

EXAMPLE B

A wettable powder which is easily dispersible in water is obtained by mixing
25 parts by weight of active substance
64 parts by weight of quartz containing kaolin as inert material
10 parts by weight of potassium lignosulfonate and
1 part by weight of sodium oleoyl-methyl-tauride as wetting and dispersing agent and grinding the mixture in a pin mill.

EXAMPLE C

A dispersion concentrate readily dispersible in water is obtained by mixing
20 parts by weight of active substance
6 parts by weight of nonylphenol polyglycol ether (10 EO)
3 parts by weight of isotridecanol polyglycol ether (8 EO) and
71 parts by weight of paraffinic mineral oil (boiling range 255° to >377° C. at atmospheric pressure)
and grinding the mixture in a ball mill to a particle size below 5 microns.

EXAMPLE D

An emulsifiable concentrate is obtained from 15 parts by weight of active substance 75 parts by weight of cyclohexanone as solvent, and 10 parts by weight of oxethylated nonyl phenol (10 EO) as emulsifier.

(C) BIOLOGICAL EXAMPLES

EXAMPLE I

Wheat plants in the three-leaf stage were strongly infested with conidia of powdery mildew of cereals (Erysiphe graminis) and then kept in the greenhouse at 20° C. and a relative atmospheric humidity of 90 to 95%. 3 Days after infestation, the plants were sprayed to the drip off with spray liquors containing the compounds indicated in Table I in concentrations of 500, 250, 125, 60, 30 and 15 mg of active substance per liter. As comparative agent Maneb was used. After a time of incubation of 10 days, the plants were examined as to their degree of infestation with mildew, which is indicated in the table in % of infested leaf area with respect to untreated but infested control plants (100% infestation).

The results are indicated in Table I.

TABLE I

| Compound of Ex. No. | leaf surface in percent infested with powdery mildew after treatment with mg of active substance per liter of spray liquor | | | | | |
|---|---|---|---|---|---|---|
| | 500 | 250 | 125 | 60 | 30 | 15 |
| 13 | 0 | 5 | 15 | 25 | | |
| 11 | 0 | 5 | 15 | 25 | | |
| 9 | 0 | 3–5 | 10 | 15 | | |
| 10 | 0 | 5 | 15 | 25 | | |
| 12 | 0–3 | 5 | 15 | 25 | | |
| 20 | 0–3 | 3 | 10 | 15 | | |
| 14 | 0–3 | 3 | 5 | 10 | | |
| 27 | 0 | 0 | 0 | 5 | 10–15 | |
| 1 | 0 | 0 | 3–5 | 10 | 15 | |
| 2 | 0 | 0 | 0 | 3–5 | 10 | |
| 35 | 0 | 0 | 0 | 0 | 5 | |
| 34 | 0 | 0 | 0 | 0 | 0–3 | 3–5 |
| 37 | 0 | 0 | 0 | 0 | 3 | 5 |
| 81 | 0 | 0 | 0 | 0 | 3 | 5 |
| 89 | 0 | 0 | 0 | 0 | 3 | 5 |
| 80 | 0 | 0 | 0 | 0 | 0 | 0 |
| 78 | 0 | 0 | 0 | 0 | 0 | 0 |
| 75 | 0 | 0 | 0 | 0–3 | 5 | 15 |
| 74 | 0 | 0 | 0 | 0 | 5 | 10 |
| 73 | 0 | 0 | 0–3 | 15–10 | 15 | 25 |
| 90 | 0 | 0 | 0 | 0 | 3 | 5 |
| Maneb* | 5 | 10 | 15 | 25 | | |
| untreated infested plants | 100 | | | | | |

*Maneb = manganous ethylene bisdithiocarbamate

EXAMPLE II

Cucumber plants of the type Delikatess in the two-leaf stage were strongly infested with a conidia suspension of cucumber mildew (Erysiphe cichoracearum). The spore suspension was allowed to dry on the plants for 30 minutes, whereupon they were transferred to the greenhouse having a temperature of 22° C. and a relative humidity of 90%. 3 Days after infestation the plants were sprayed to the drip off with spray liquors of the compounds listed in Table II in the indicated concentrations. As comparative agent Maneb was used. The plants were inspected as to their degree of infestation 10 days after the treatment. The degree of infestation is expressed in % of infested leaf area, relative to untreated but infested control plants (100% infestation). The results are indicated in Table II.

TABLE II

| Compound of Ex. No. | leaf surface in percent infested with cucumber mildew after treatment with mg of active substance per liter of spray liquor | | | | | |
|---|---|---|---|---|---|---|
| | 500 | 250 | 125 | 60 | 15 | 8 |
| 13 | 0 | 3–5 | 10 | 15 | | |
| 11 | 0 | 3–5 | 5–10 | 15 | | |
| 9 | 0 | 3–5 | 10 | 15–25 | | |
| 10 | 0 | 3–5 | 15 | 25 | | |
| 12 | 0 | 3 | 3 | 5–10 | | |
| 20 | 0–3 | 5 | 10 | 15 | | |
| 14 | 0 | 0–3 | 5 | 10–15 | | |
| 25 | 0 | 0–3 | 5 | 10–15 | | |
| 27 | 0 | 0 | 0 | 0–3 | 5–10 | |
| 1 | 0 | 0 | 0 | 0 | 0–3 | |
| 2 | 0 | 0 | 0 | 0 | 3 | |
| 35 | 0 | 0 | 0 | 0 | 0 | 5 |
| 90 | 0 | 0 | 0 | 0 | 3 | |
| 81 | 0 | 0 | 0 | 0 | 3 | |
| 89 | 0 | 0 | 0 | 0 | 3 | |
| 80 | 0 | 0 | 0 | 0 | 0 | |
| 78 | 0 | 0 | 0 | 0 | 0 | |
| 75 | 0 | 0 | 0 | 0 | 0–3 | |
| 74 | 0 | 0 | 0 | 0 | 0–3 | |
| 73 | 0 | 0 | 0 | 0 | 0–3 | |
| Maneb* | 15 | 25 | 35 | 60 | 100 | |
| untreated infested plants | 100 | | | | | |

*Maneb = manganous ethylene bisdithiocarbamate

EXAMPLE III

Cucumber plants of the type Delikatess in the two-leaf stage were strongly infested with a conidia suspension of Benomyl-resistant cucumber mildew (Erysiphe cichoracearum). The spore suspension was allowed to dry on the plants for 30 minutes, whereupon they were transferred to the greenhouse having a temperature of 22° C. and a relative humidity of 90%. 3 Days after infestation the plants were sprayed to the drip off with spray liquors of the compounds listed in Table III in the indicated concentrations. As comparative agent Maneb was used. The plants were inspected as to their degree of infestation 10 days after the treatment. The degree of infestation is expressed in % of infested leaf area, relative to untreated but infested control plants (100% infestation). The results are indicated in Table III.

TABLE III

| Compound of Ex. No. | leaf area infested with cucumber mildew (strain resistant to Benomyl) in % with mg of active substance per liter of spray liquor | | | | | |
|---|---|---|---|---|---|---|
| | 500 | 250 | 125 | 60 | 15 | 7 |
| 13 | 0 | 3–5 | 10 | 15 | | |
| 11 | 0 | 5 | 5–10 | 15 | | |
| 9 | 0 | 5 | 10 | 15 | | |
| 10 | 0 | 3–5 | 15 | 25 | | |
| 12 | 0 | 0 | 0–3 | 15–25 | | |
| 20 | 0 | 0–3 | 3–5 | 15 | | |
| 14 | 0 | 3 | 5–10 | 15 | | |
| 25 | 0 | 0 | 3–5 | 5–10 | | |
| 27 | 0 | 0 | 0 | 3 | 5 | 10 |
| 1 | 0 | 0 | 0 | 0 | 3–5 | 5 |
| 2 | 0 | 0 | 0 | 0 | 3–5 | 5 |
| 35 | 0 | 0 | 0 | 0 | 0 | 3 |
| 90 | 0 | 0 | 0 | 0 | 3–5 | |
| 81 | 0 | 0 | 0 | 0 | 3 | |
| 89 | 0 | 0 | 0 | 0 | 3 | |
| 80 | 0 | 0 | 0 | 0 | 0 | |
| 78 | 0 | 0 | 0 | 0 | 0–3 | |
| 75 | 0 | 0 | 0 | 0 | 3–5 | |
| 74 | 0 | 0 | 0 | 0 | 3–5 | |
| 73 | 0 | 0 | 0 | 0 | 3 | |
| Maneb* | 15 | 25 | 35 | 60 | 100 | 100 |
| untreated infested plants | 100 | | | | | |

*Maneb = manganous ethylene bisdithiocarbamate

EXAMPLE IV

Barley plants in the three-leaf stage were strongly infested with conidia of powdery mildew of cereals (Erysiphe graminis sp. hordei) and kept in the greenhouse at 20° C. and a relative humidity of 90 to 95%. Three days after infestation the plants were sprayed to the drip off with spray liquors of the compounds listed in Table IV in concentrations of 500, 250, 125, 60 and 30 mg per liter of spray liquor. Maneb was used for comparison. After a time of incubation of 10 days, the plants were examined as to the degree of infestation with mildew. The degree of infestation is expressed in percent of infested leaf area relative to untreated but infested control plants (100% infestation). The results are summarized in Table IV.

TABLE IV

| Compound of Ex. No. | leaf surface in percent infested with powdery mildew after treatment with mg of active substance per liter of spray liquor | | | | |
|---|---|---|---|---|---|
| | 500 | 250 | 125 | 60 | 30 |
| 13 | 0 | 5–10 | 15 | 25 | |
| 11 | 0 | 3 | 5–10 | 15 | |
| 9 | 0 | 3–5 | 10 | 25 | |
| 10 | 0 | 3 | 10–15 | 25 | |
| 8 | 0–3 | 10 | 15 | 25 | |
| 12 | 0 | 5–10 | 15 | 25 | |
| 20 | 0–3 | 5–10 | 15 | 25 | |
| 14 | 0 | 5–10 | 15 | 25 | |
| 25 | 0–3 | 10–15 | 25 | 35 | |
| 27 | 0 | 0 | 0 | 3–5 | 10 |
| 1 | 0 | 0 | 0 | 0 | 3–5 |
| 2 | 0 | 0 | 0 | 0 | 3–5 |
| 35 | 0 | 0 | 3 | 3–5 | 5 |
| 34 | 0 | 0 | 0–3 | 5–10 | 15 |
| 37 | 0 | 0–3 | 3–5 | 10 | 15–25 |
| 90 | 0 | 0 | 0 | 0 | 3 |
| 81 | 0 | 0 | 0 | 0 | 0–3 |
| 89 | 0 | 0 | 0 | 0 | 3–5 |
| 80 | 0 | 0 | 0 | 0 | 0 |
| 78 | 0 | 0 | 0 | 0 | 0 |
| 75 | 0 | 0 | 0 | 0–3 | 5 |
| 74 | 0 | 0 | 0 | 0–3 | 3–5 |
| 73 | 0 | 0 | 0 | 0–3 | 3 |
| Maneb* | 25 | 35 | 60 | 100 | 100 |
| untreated infested plants | 100 | | | | |

*Maneb = manganous ethylene bisdithiocarbamate

EXAMPLE V

Apple stocks of the type EM IX in the four-leaf stage were strongly infested with a conidia suspension of powdery mildew of apple (Podosphaera leucotricha). The plants were cept for 16 hours in a climatic chamber having a temperature of 20° C. and a relative humidity of about 100% and then transferred to the greenhouse where the temperature was 22° C. and the relative humidity amounted to 85%. Three days after infestation the plants were sprayed to the drip off with the compounds listed in Table V in the indicated concentrations. Maneb was used for comparison. After 2 to 3 weeks the plants were inspected as to the degree of infestation with mildew, which is expressed in the table in % of infested leaf surface, relative to untreated but infested control plants (=100%). The results are summarized in Table V.

TABLE V

| Compound of Ex. No. | leaf surface infested with apple mildew in % with mg of active substance per liter of spray liquor | | | |
|---|---|---|---|---|
| | 1000 | 500 | 250 | 125 |
| 12 | 0 | 0–3 | 5 | 15 |
| 14 | 0 | 0–3 | 5 | 25 |
| 27 | 0–3 | 3 | 5 | 15 |
| 1 | 0–3 | 3 | 5–10 | 15–25 |
| 2 | 0 | 0–3 | 3–5 | 5 |
| 35 | 0 | 0–3 | 5 | 5 |
| Maneb* | 25 | 35 | 60 | 100 |
| untreated infested plants | 100 | | | |

*Maneb = manganous ethylene bisdithiocarbamate

EXAMPLE VI (growth inhibition)

In tray tests in the greenhouse young plants of cereals (wheat, barley and rye) in the three-leaf stage were sprayed to the drip off with spray liquors of the compounds listed in Table VI in the indicated concentrations (kg/hectare). 2-Chloroethyltrimethylammonium chloride, maleic acid hydrazide and succinic acid 2,2-dimethylhydrazide were used for comparison. When the untreated control plants had reached a height of growth of about 55 cm, the growth of all plants was measured and the inhibition was calculated in percent of the growth of the control plants. In addition, the phytotoxic effect of the compounds was examined. The results are indicated in Table VI, in which an inhibition of growth of 100% means no growth at all while 0% inhibition corresponds to the growth of the untreated control plants.

TABLE VI

| Compound of Ex. No. | Inhibition of growth in cereals | | | |
|---|---|---|---|---|
| | concentration of of active substance kg/ha | % inhitition of growth | | phytotoxic effect |
| | | wheat | barley | rye | |
| 127 | 2.5 | 33 | 29 | 26 | no damage |
| | 1.25 | 30 | 28 | 10 | |
| comparison (2-chloroethyl)-trimethyl-ammonium chloride | 2.5 | 27 | 8 | 10 | no damage |
| | 1.25 | 23 | 0 | 0 | |
| comparison maleic acid hydrazide | 2.5 | 37 | 35 | 38 | heavy damage |
| | 1.25 | 20 | 20 | 29 | |
| comparison succinic acid 2,2-dimethyl-hydrazide | 2.5 | 0 | 0 | 0 | no damage |
| | 1.25 | 0 | 0 | 0 | |

What is claimed is:
1. A 1,2,4-triazole derivative of the formula I

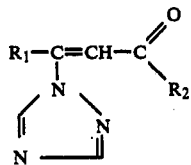 (I)

in which
- R$_1$ denotes methyl or phenyl optionally substituted by halogen, (C$_1$-C$_4$)alkyl or (C$_1$-C$_4$)-alkoxy, and
- R$_2$ denotes the group R$_3$O— in which R$_3$ is alkyl, having up to 12 carbon atoms, which may be substituted additionally by halogen, (C$_1$-C$_4$)alkoxy or alkoxycarbonyl having up to 8 carbon atoms; or is alkinyl having up to 3 carbon atoms; or is cycloalkyl having up to 6 carbon atoms and optionally substituted additionally by (C$_1$-C$_4$)alkyl; or is phenyl optionally substituted by halogen or F$_3$C—, or
- R$_2$ denotes

in which R$_4$ is hydrogen or (C$_1$-C$_4$)-alkyl optionally substituted by alkoxycarbonyl having up to 8 carbon atoms, and R$_5$ is (C$_1$-C$_4$)alkyl or phenyl optionally substituted by halogen, F$_3$C—, (C$_1$-C$_4$)alkyl, (C$_1$-C$_4$)alkoxy, phenoxy or halophenoxy.

2. A pesticidal composition having fungicidal activity comprising a carrier or suitable auxiliary and as an active ingredient a compound as defined in claim 1.

3. The composition of claim 2 wherein said compound is present in an amount of from 2 to 95% by weight of said composition.

4. A pesticidal composition having plant growth regulating activity comprising a carrier or suitable auxiliary and as an active ingredient a compound defined in claim 1.

5. The composition of claim 4 wherein said compound is present in an amount of from 2 to 95% by weight of said composition.

6. A method of controlling plant infestation which comprises treating said plants with a compound as defined in claim 1.

7. A method of regulating plant growth which comprises treating said plants with a compound as defined in claim 1.

8. A method of inhibiting growth in cereals which comprises treating said cereals with a compound as defined in claim 1.

* * * * *